(12) United States Patent
Savory (10) Patent No.: US 7,906,518 B2
(45) Date of Patent: Mar. 15, 2011

(54) THERAPEUTIC COMPOUNDS

(75) Inventor: Edward D. Savory, Great Cambourne (GB)

(73) Assignee: CBT Development Limited (GB)

(\*) Notice: Subject to any disclaimer, the term of this patent is extended or adjusted under 35 U.S.C. 154(b) by 751 days.

(21) Appl. No.: 11/823,335

(22) Filed: Jun. 26, 2007

(65) Prior Publication Data

US 2008/0027081 A1 Jan. 31, 2008

Related U.S. Application Data

(60) Provisional application No. 60/837,308, filed on Aug. 11, 2006.

(30) Foreign Application Priority Data

Jun. 27, 2006 (SE) .................................... 0601396-5

(51) Int. Cl.
*C07D 473/34* (2006.01)
*C07D 473/18* (2006.01)
*A61K 31/52* (2006.01)
*A61K 31/522* (2006.01)
*A61P 19/02* (2006.01)
*A61P 29/00* (2006.01)

(52) U.S. Cl. ...................... 514/263.24; 544/276; 544/277

(58) Field of Classification Search ............. 514/263.34; 544/276, 277
See application file for complete search history.

(56) References Cited

U.S. PATENT DOCUMENTS

| | | | | |
|---|---|---|---|---|
| 6,117,878 | A * | 9/2000 | Linden ..................... | 514/263.34 |
| 6,894,021 | B2 * | 5/2005 | Belardinelli et al. ............. | 514/1 |
| 7,553,823 | B2 * | 6/2009 | Zablocki et al. ................ | 514/46 |
| 2002/0147174 | A1 * | 10/2002 | Jones et al. ..................... | 514/46 |
| 2003/0040502 | A1 * | 2/2003 | Salzman et al. ................ | 514/45 |
| 2004/0180948 | A1 * | 9/2004 | Linden et al. ................ | 514/447 |
| 2004/0266722 | A1 * | 12/2004 | Devos et al. ..................... | 514/46 |
| 2005/0059683 | A1 * | 3/2005 | Zablocki et al. ........... | 514/263.2 |
| 2005/0159388 | A1 * | 7/2005 | Plourde et al. .................. | 514/45 |
| 2005/0261236 | A1 * | 11/2005 | Okusa et al. ..................... | 514/46 |
| 2007/0093446 | A1 * | 4/2007 | Douglass et al. ............... | 514/47 |
| 2007/0123544 | A1 * | 5/2007 | Plourde et al. ............ | 514/261.1 |
| 2007/0208040 | A1 * | 9/2007 | Elzein et al. ............... | 514/260.1 |
| 2007/0219221 | A1 * | 9/2007 | Zeng et al. .................. | 514/263.2 |
| 2007/0232626 | A1 * | 10/2007 | Jacobson et al. ......... | 514/263.37 |
| 2007/0274910 | A1 * | 11/2007 | Wilson et al. ................. | 424/1.65 |
| 2007/0299089 | A1 * | 12/2007 | Belardinelli et al. ....... | 514/263.2 |
| 2008/0027022 | A1 * | 1/2008 | Linden et al. .................... | 514/46 |
| 2008/0176858 | A1 * | 7/2008 | Beauglehole et al. ... | 514/252.16 |
| 2008/0214581 | A1 * | 9/2008 | Allen et al. ................ | 514/263.2 |
| 2008/0242673 | A1 * | 10/2008 | Moorman ................ | 514/252.16 |
| 2008/0262001 | A1 * | 10/2008 | Kranenburg et al. ..... | 514/263.22 |
| 2008/0312160 | A1 * | 12/2008 | Guerrant et al. ................ | 514/19 |
| 2009/0012035 | A1 * | 1/2009 | Jacobson et al. ................ | 514/46 |
| 2009/0054476 | A1 * | 2/2009 | Goblyos et al. ............... | 514/293 |
| 2009/0081764 | A1 * | 3/2009 | Pausch et al. ............. | 435/254.2 |
| 2009/0099212 | A1 * | 4/2009 | Zablocki et al. ........... | 514/263.2 |
| 2009/0123510 | A1 * | 5/2009 | Cronstein et al. ............. | 424/422 |
| 2009/0156544 | A1 * | 6/2009 | Elzein et al. ..................... | 514/46 |
| 2009/0170805 | A1 * | 7/2009 | Tan et al. ......................... | 514/46 |
| 2009/0181920 | A1 * | 7/2009 | Watkins et al. .................. | 514/45 |
| 2009/0203689 | A1 * | 8/2009 | Dhalla et al. ............... | 514/234.2 |
| 2009/0247745 | A1 * | 10/2009 | Aranyi et al. .................... | 544/94 |
| 2009/0325967 | A1 * | 12/2009 | Fairhurst et al. .............. | 514/245 |

FOREIGN PATENT DOCUMENTS

| | | |
|---|---|---|
| EP | 0997473 A1 | 5/2000 |
| EP | 1491201 A1 | 12/2004 |
| WO | WO-2004052377 A1 | 6/2004 |
| WO | WO-2004078183 A1 | 9/2004 |
| WO | WO-2004078184 A1 | 9/2004 |
| WO | WO-2005084653 A2 | 9/2005 |

OTHER PUBLICATIONS

Keeling, Suzanne E. et al., "The Discovery and Synthesis of Highly Potent, A2a Receptor Agonists," Bioorganic & Medicinal Chemistry Letters 2000, vol. 10, p. 403-406.

Doytchinova, I. et al., "Adenosine A2A receptor agonists: CoMFA-based selection of the most predictive conformation," SAR and QSAR in Environmental Research 2002, vol. 13, No. 2, p. 227-235.

\* cited by examiner

*Primary Examiner* — Mark L Berch

(74) *Attorney, Agent, or Firm* — Edwards Angell Palmer & Dodge LLP; Jeffrey D. Hai; Weiying Yang (57) ABSTRACT

The invention relates to a method of improving oral drug absorption of adenosine analogues by the use of 2',3'-methylidene acetal adenosine pro-drugs and to the use of these pro-drugs as medicaments. The invention further relates to compounds that are pro-drugs of adenosine receptor agonists, and to their use as therapeutic compounds, in particular as analgesic or anti-inflammatory compounds, or as disease modifying antirheumatic drugs (DMARDs), and to methods of preventing, treating or ameliorating pain or inflammation using these compounds.

3 Claims, 1 Drawing Sheet

FIGURE 1

THERAPEUTIC COMPOUNDS

CROSS-REFERENCE TO RELATED APPLICATIONS

This application claims benefit of Swedish application No. 0601396-5 filed Jun. 27, 2006 and U.S. application 60/837, 308 filed Aug. 11, 2006, the entire contents of each is herein incorporated by reference.

TECHNICAL FIELD

The invention relates to a method of improving oral drug absorption of adenosine analogues by the use of 2',3'-methylidene acetal adenosine pro-drugs and to the use of these pro-drugs as medicaments. The invention further relates to compounds that are pro-drugs of adenosine receptor agonists, and to their use as therapeutic compounds, in particular as analgesic or anti-inflammatory compounds, or as disease modifying antirheumatic drugs (DMARDs), and to methods of preventing, treating or ameliorating pain or inflammation using these compounds.

BACKGROUND ART

Adenosine is a ubiquitous local hormone/neurotransmitter that acts on four known receptors, the adenosine A1, A2A, A2B and A3 receptors. Adenosine generally serves to balance the supply and demand of energy in tissues. For example, in the heart released adenosine slows the heart by an A1 receptor mediated action in the nodes and atria (Belardinelli, L & Isenberg, G Am. J. Physiol. 224, H734-H737), while simultaneously dilating the coronary artery to increase energy (i.e. glucose, fat and oxygen) supply (Knabb et al, Circ. Res. (1983) 53, 33-41). Similarly, during inflammation adenosine serves to inhibit inflammatory activity, while in conditions of excessive nerve activity (e.g. epilepsy) adenosine inhibits nerve firing (Klitgaard et al, Eur J. Pharmacol. (1993) 242, 221-228). This system, or a variant on it, is present in all tissues.

Adenosine itself can be used to diagnose and treat supraventricular tachycardia. Adenosine A1 receptor agonists are known to act as powerful analgesics (Sawynok, J. Eur J Pharmacol. (1998) 347, 1-11; Giffin et al, (2003) 23, 4, 287-292). A2a agonists have recently been shown to give significant pain relief in conditions of increased pain sensitivity (such as neuropathic and inflammatory hyperalgesia) (WO 2004/052377; WO 2004/078183; WO 2004/078184; WO 2005/084653) and are known to have anti-inflammatory activity (see, for example U.S. Pat. No. 5,877,180; WO 99/34804; Linden et al, Expert Opin. Investig. Drugs (2005) 14, 7, 797-806; Sitkovsky et al, TRENDS in Immunology (2005) 26, 6, 299-304; Linden et al, Journal of Immunology (2006) 117, 2765-2769; Cronstein et al (2004) 25, 1, 33-39). In experimental animals, A2A receptor agonists have been shown to be effective against a wide variety of conditions including sepsis (Linden et al, The Journal of Infectious Diseases (2004) 189, 1897-1904), arthritis (Cohen et al, J. Orthop. Res. (2005) 23, 5, 1172-1178; Cohen et al, J. Orthop. Res. (2004) 22, 2, 427-435), and ischaemia/reperfusion injury arising from renal, coronary or cerebral artery occlusion (see, for example Day et al, J. Clin. Invest, (2003) 112, 883-891; Linden et al, Am. J. Physiol. Gastrointest. Liver Physiol. (2004) 286, G285-G293; Linden et al, Am J. Physiol. (1999) 277, F404-F412; Schlack et al, J. Cardiovasc. Pharmacol. (1993) 22, 89-96; Zu et al, J. Cardiovasc. Pharmacol. (2005) 46, 6, 794-802; Linden et al, Am J. Physiol. Heart Circ. Physiol. (2005) 288, 1851-1858; Kennedy et al, Current Opinion in Investigational Drugs (2006) 7, 3, 229-242). The common factor in these conditions is a reduction in the inflammatory response caused by the inhibitory effect of this receptor on most, if not all, inflammatory cells. A2a agonists are also known to promote wound healing (Montesinos, Am. J. Pathol. (2002) 160, 2009-2018).

However, the ubiquitous distribution of adenosine receptors means that administration of adenosine receptor agonists causes adverse side effects. This has generally precluded the development of adenosine-based therapies. Selective A1 receptor agonists cause bradycardia. A2a receptor agonists cause widespread vasodilation with consequent hypotension and tachycardia. The first selective A2A receptor agonist (2-[4-(2-carboxyethyl)phenylethylamino]-5'-N-ethylcarboxamidoadenosine, or CGS21680), was tested in a Phase 2A clinical trial as a potential anti-hypertensive. However, administration of this compound caused a large fall in blood pressure and consequent increase in cardiac output. This has prevented use of CGS21680 as a medicament. Webb et al. (J. Pharmacol Exp Ther (1991) 259, 1203-1212), Casati et al, (J Pharmacol Exp Ther (1995) 275(2):914-919), and Bonnizone et al, (Hypertension. (1995) 25, 564-9) show that selective A2A adenosine receptor agonists cause hypotension and tachycardia. The degree of tachycardia induced is sufficient to preclude their use as medicaments. Alberti et al, (J Cardiovasc Pharmacol. (1997) September; 30(3):320-4) discloses that selective A2A adenosine receptor agonists are potent vasodilators that reduce blood pressure and induce marked increments in heart rate and plasma renin activity. These side effects preclude their use as medicaments.

U.S. Pat. No. 5,877,180 relates to agonists of A2A adenosine receptors which are stated to be effective for the treatment of inflammatory diseases. The preferred agonists, WRC0090 and SHA 211 (WRC0474), are disclosed to be more potent and selective than previously reported adenosine analogs such as CGS21680 and CV1808. Administration of SHA 211 or WRC0090 is considered to reduce the possibility of side effects mediated by the binding of the analogs to other adenosine receptors. However, only in vitro data relating to the activity of SHA 211 is included. There is no demonstration that any of the compounds described could be therapeutically effective in vivo without causing serious side effects. Although side effects mediated by the binding of potent and selective adenosine A2A receptor agonists to other adenosine receptors is expected to be reduced by use of such agonists, the ubiquitous distribution of adenosine receptors means that these compounds would still be expected to activate adenosine A2A receptors in normal tissue and, therefore, cause serious side effects (such as hypotension and reflex tachycardia).

U.S. Pat. No. 3,936,439 discloses use of 2,6-diaminonebularine derivatives as coronary dilating and/or platelet aggregation inhibitory agents for mammals. In vivo data in dogs is included to support the coronary dilating action of $N^2$-Phenyl-2,6-diaminonebularine, $N^2$-Cyclohexyl-2,6-diaminonebularine, $N^2$-(p-methoxyphenyl)-2,6-diaminonebularine, and $N^2$-Ethyl-2,6-diaminonebularine, and in vitro data supports the platelet aggregation inhibitory action of $N^2$-Phenyl-2,6-diaminonebularine, $N^2$-cyclohexyl-2,6-diaminonebularine, 2,6-Diaminonebularine, and $N^2$-Ethyl-2,6-diaminonebularine. FR 2162128 (Takeda Chemical Industries, Ltd) discloses that adenosine derivatives (including 2-alkoxy adenosine derivatives comprising a lower alkyl group of not less than two carbon atoms) have hypotensive and coronary vasodilatory activity. In vivo data in dogs supports the coronary vasodilatory activity of 2-n-pentyloxyadenosine, 2-(β-hydroxyethoxy)-adenosine, and 2-phenoxyadenosine. However, there is no demonstration in U.S. Pat. No. 3,936,439 or FR 2162128 that any of the compounds described could be administered without causing serious side effects.

Ribeiro et al, (Progress in Neurobiology 68 (2003) 377-392) is a review of adenosine receptors in the nervous system. It is stated in the concluding remarks of this article (on page 387, right column, lines 4-10 of section 8) that "as noted a long time ago, activation of adenosine receptors at the periphery is associated with hypotension, bradycardia and hypothermia [ ... ] These side effects have so far significantly limited the clinical usefulness of adenosine receptor agonists".

There is, therefore, a need to provide adenosine receptor agonists that can be administered with minimal side effects.

Certain aspects of the invention relate to the treatment of pain. Pain has two components, each involving activation of sensory neurons. The first component is the early or immediate phase when a sensory neuron is stimulated, for instance as the result of heat or pressure on the skin. The second component is the consequence of an increased sensitivity of the sensory mechanisms innervating tissue which has been previously damaged. This second component is referred to as hyperalgesia, and is involved in all forms of chronic pain arising from tissue damage, but not in the early or immediate phase of pain perception.

Thus, hyperalgesia is a condition of heightened pain perception caused by tissue damage. This condition is a natural response of the nervous system apparently designed to encourage protection of the damaged tissue by an injured individual, to give time for tissue repair to occur. There are two known underlying causes of this condition, an increase in sensory neuron activity, and a change in neuronal processing of nociceptive information which occurs in the spinal cord. Hyperalgesia can be debilitating in conditions of chronic inflammation (e.g. rheumatoid arthritis), and when sensory nerve damage has occurred (i.e. neuropathic pain).

Two major classes of analgesics are known: (i) non steroidal anti-inflammatory drugs (NSAIDs) and the related COX-2 inhibitors; and (ii) opiates based on morphine. Analgesics of both classes are effective in controlling normal, immediate or nociceptive pain. However, they are less effective against some types of hyperalgesic pain, such as neuropathic pain. Many medical practitioners are reluctant to prescribe opiates at the high doses required to affect neuropathic pain because of the side effects caused by administration of these compounds (such as restlessness, nausea, and vomiting), and the possibility that patients may become addicted to them. NSAIDs are much less potent than opiates, so even higher doses of these compounds are required. However, this is undesirable because these compounds cause irritation of the gastro-intestinal tract.

There is also a need to provide analgesics, particularly anti-hyperalgesics, which are sufficiently potent to control pain perception in neuropathic and other hyperalgesic syndromes, and which do not have serious side effects or cause patients to become addicted to them.

It has recently become apparent (WO 2004/052377; WO 2004/078183; WO 2004/078184; WO 2005/084653) that some adenosine agonists (e.g. spongosine) are effective analgesics at doses as much as one hundred times lower than would be expected to be required based on the known affinity of this compound for adenosine receptors. At such doses, spongosine and related compounds do not cause the significant side effects associated with adenosine receptor activation. The underlying mechanism behind these observations appears to be that these compounds have increased affinity for adenosine receptors at pH below pH 7.4. It is believed that this property explains the surprising activity of these compounds at low doses. The Applicant has been able to identify certain other compounds that also have increased affinity for adenosine receptors at reduced pH. It is thought that these compounds can be used as medicaments without causing serious side effects. However a significant proportion of these compounds exhibit poor oral bioavailability and short plasma half lives, thus limiting their usefulness as therapeutics.

Spongosine was first isolated from the tropical marine sponge, *Cryptotethia crypta* in 1945 (Bergmann and Feeney, J. Org. Chem. (1951) 16, 981, Ibid (1956) 21, 226), and was the first methoxypurine found in nature. It is also known as 2-methoxyadenosine, or 9H-purin-6-amine, 9-α-D-arabinofuranosyl-2-methoxy. The first biological activities of spongosine were described by Bartlett et al, (J. Med. Chem. (1981) 24, 947-954). Spongosine (and other compounds) was tested for its skeletal muscle-relaxant, hypothermic, cardiovascular and anti-inflammatory effects in rodents following oral administration (anti-inflammatory activity was assessed by inhibition of carageenan-induced oedema in a rat paw). Spongosine caused 25% inhibition of carageenan-induced inflammation in rats at 20 mg/kg po. However, reductions in mean blood pressure (41%), and in heart rate (25%) were also observed after administration of this compound at this dose.

The affinity of spongosine for the rat adenosine A1 and A2A receptors has been determined. The $K_d$ values obtained (in the rat) were 340 nM for the A1 receptor and 1.4 μM for the A2A receptor, while the $EC_{50}$ value for stimulation of the rat A2A receptor was shown to be 3 μM (Daly et al, Pharmacol. (1993) 46, 91-100). In the guinea pig, the efficacy of spongosine was tested in the isolated heart preparation and the EC50 values obtained were 10 μM and 0.7 μM for the adenosine A1 and A2A receptors, respectively (Ueeda et al, J Med Chem (1991) 34, 1334-1339). Because of the low potency and poor receptor selectivity of this compound it was largely ignored in favor of more potent and receptor selective adenosine receptor agonists.

The use of nucleoside analogues in the treatment of diseases is often limited by poor oral absorption (Han et al, Pharm. Res. (1998) 15(8), 1154-9). Nucleosides are poorly soluble, polar molecules, and these properties make them poorly permeable to systemic membranes, such as the blood-brain barrier and the cellular membranes that provide access to the drugs' targets (Kling, Modern Drug Discovery (1999) 2(3), 26-36). Thus, oral administration of nucleoside drugs often results in poor or irreproducible in vivo efficacy as a result of a limited or variable concentration of the drug at the site of action. The design and synthesis of new nucleoside analogues therefore remains a very active area of research, with the goal of discovering drugs with optimal oral bioavailability (Dresser et al, Drug Metabolism and Disposition (2000) 28, 9, 1135-40).

Numerous research groups have attempted to solve the problem of poor oral bioavailability of nucleoside drugs by employing a pro-drug of the chosen bioactive species. A pro-drug is a drug which has been chemically modified and may be biologically inactive at its site of action, but which will be degraded or modified by one or more enzymatic or in vivo processes to the bioactive form.

The design of nucleoside pro-drugs has focused on improving oral bioavailabilty by the targeting of nucleoside or peptide transporters, through exploitation of enzymatic processes such adenosine deaminase activation, or by the appending of specific substituents to the sugar moiety of the nucleoside, which aid membrane permeation and are then cleaved in vivo to release the active species.

Various pro-drugs of antivirals have been attempted. Most notably, U.S. Pat. No. 4,957,924 discloses various therapeutic esters of the antiherpetic agent, acyclovir. Valacyclovir, the L-valyl ester of Acyclovir, is an oral prodrug that undergoes rapid and extensive first-pass metabolism to yield Acyclovir and the amino acid L-valine. The bioavailability of Acyclovir from oral Valacyclovir is considerably greater than that achieved after oral Acyclovir administration. Oral administration of Valacyclovir produced a greater increase in urinary excretion of Acyclovir (63%), compared with oral administration of Acyclovir itself (19%) (Perry and Faulds Drugs (1996) 52, 754-72). This increase in oral bioavailability has been attributed to interaction of the L-valyl ester moiety of Valacyclovir with the peptide transporter hPEPT1 (Sawada et al, J. Pharmacol. Exp. Ther. (1999) 291, 2, 705-9; Anand et al, J. Pharmacol. Exp. Ther. (2003) 304, 781). An analogous strategy has been used to increase the oral bioavailability of Zidovudine (AZT) (Han et al, Pharm. Res. (1998) 15(8), 1154-9).

Similarly, WO 01/96353 relates to 3'-prodrugs of 2'-deoxy-β-L-nucleosides for the treatment of hepatitis B virus, that are amino acid esters including valyl and alkyl esters, specifically 3'-L-amino acid ester and 3',5'-L-diamino acid esters. For example, in cynamalogous monkeys, the 3',5'-divaline ester pro-drug of 2'-deoxy-β-L-cytidine released 2'-deoxy-β-L-cytidine in vivo with 73% oral bioavailability and a 2.28 h (po) half-life, in comparison to an oral bioavailability of 18% and a half-life of 2.95 h (po) following dosing of 2'-deoxy-β-L-cytidine itself.

In an alternative approach, adenosine deaminase activation of pro-drugs to the active species has been exploited. For example, Viramidine has been shown to act as a pro-drug to the chronic hepatitis C drug, Ribavarin. Viramidine is predominantly converted by adenosine deaminase to Ribavarin in the liver and this liver-targeting property has being exploited to circumvent haemolytic anaemia side effects caused by Ribavarin itself. Thus, after multiple oral dosing of [$^{14}$C]Ribavarin or [$^{14}$C]Viramidine to monkey, Viramidine yielded three times the drug level in the liver but only half in red blood cells compared to Ribavarin (Lin et al, Antiviral chemistry & chemotherapy (2003) 14, 145-152; Wu et al, Journal of Antimicrobial Chemotherapy (2003) 52, 543-6).

WO 00/71558 discloses the use of pro-drugs that are esters of N6-oxa, thia, thioxa and azacycloalkyl substituted adenosine derivatives that are selective adenosine A1 receptor agonists. Although an increase in observed in vivo efficacy (fall in heart rate) was observed using this strategy, no data is presented proving this to be a result of any increase in oral bioavailability or effective half-life. Sommadossi et al. (WO 2004/003000) have disclosed 2' and 3'-pro-drugs of 1', 2', 3' or 4', SS-D or SS-L, branched nucleosides for treating flaviviridae infections but similarly have not demonstrated that these pro-drugs improve oral bioavailabilty or half-life. Dalpiaz et al (Acta Technologiae et Legis Medicamenti (2002) 13, 49 and Pharm. Res. (2001) 18, 531) have reported stability data of 5'-ester pro-drugs of 6-cyclopentylaminoadenosine (CPA) in whole blood and plasma.

DISCLOSURE OF THE INVENTION

The present invention provides the use in therapy of novel 2',3'-methylidene acetal pro-drugs of adenosine derivatives that are converted within the mammalian body to become therapeutically useful adenosine receptor agonists or antagonists. The 2',3'-methylidene acetal functionality, despite being only a small structural modification to the nucleoside template, can surprisingly cause a significant increase in both the oral bioavailability and oral half-life of the pro-drugged adenosine derivative (active metabolite) reaching the receptor target, in comparison to the oral bioavailability and oral half-life that is observed following oral dosing of the metabolite itself (i.e. when this pro-drug strategy is not employed).

In a first preferred aspect, the invention provides the use of a compound of Formula I, or a pharmaceutically acceptable salt thereof,

I wherein:
R1 is adenine, which is unsubstituted or substituted with 1-3 substituents independently selected from halogen, OH, OR2, NR2R3, CN, SR2 or R2;
R2 and R3 are independently selected from H, $C_{1-6}$-alkyl, $C_{3-8}$-cycloalkyl, aryl or heterocyclyl, each optionally substituted with 1-3 substituents independently selected from halogen, OH, $NH_2$, CN or $CF_3$;
in the manufacture of a medicament for use against a medical condition that can be improved or prevented by agonism or antagonism of an adenosine receptor.

Preferably, the said compound of Formula I is having the formula II, or a pharmaceutically acceptable salt thereof,

II wherein R1 is as described for Formula I.

In a preferred aspect of the invention, the said medical condition can be improved or prevented by agonism of an adenosine receptor. In particular, the said medical condition can be associated with pain, inflammation, and/or arthropathy.

In a further aspect, the invention provides the use of a compound of Formula (I) or (II) in the manufacture of an improved medicament having increased bioavailability and/or half-life in comparison with a second medicament, said second medicament having as active ingredient a compound of Formula IV, or a pharmaceutically acceptable salt thereof,

IV wherein R1 is as defined for Formula I, and wherein R1 of the second medicament is the same as R1 of the improved medicament.

In another aspect, the invention provides a method of preventing, treating, or ameliorating a medical condition that can be prevented or improved by agonism or antagonism of an adenosine receptor, which comprises administering a compound of the Formula I or II, wherein R1, R2 and R3 are as defined above, to a subject in need of such prevention, treatment, or amelioration. In a preferred aspect of the invention, the said medical condition can be improved or prevented by agonism of an adenosine receptor. In particular, the said medical condition can be associated with pain, inflammation, and/or arthropathy.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In yet another aspect, the invention provides a method for increasing bioavailability and/or half-life of a compound having the Formula IV, or a pharmaceutically acceptable salt thereof,

IV wherein R1 is as defined for Formula I, said method comprising substituting 2'-OH and 3'-OH in the ribose moiety to form a 2'3'-O-methylidene acetal ring.

In another aspect, the invention provides a compound having the Formula III, or a pharmaceutically acceptable salt thereof,

III wherein R4 is selected from OR2, NR2R3, CN, SR2 or R2; wherein R2 and R3 are as defined for Formula I. R4 can preferably be OMe, OCH$_2$CHF$_2$, (2,5-difluorophenoxy), (3-(4-(trifluoromethyl)phenyl)phenoxy, or 3,5-bis(trifluoromethyl)phenyl.

Preferred compounds of Formula III include:
[(3aR,4R,6R,6aR)-6-(6-amino-2-methoxy-9H-purin-9yl) tetrahydrofuro[3,4-d][1,3]dioxol-4-yl]methanol;
[(3aR,4R,6R,6aR)-6-(6-amino-2-(2,2-difluoroethoxy)-9H-purin-9-yl)tetrahydrofuro[3,4-d][1,3]dioxol-4-yl]methanol;
[(3aR,4R,6R,6aR)-6-(6-amino-2-(2,5-difluorophenoxy)-9H-purin-9-yl)tetrahydrofuro[3,4-d][1,3]dioxol-4-yl] methanol;
[(3aR,4R,6R,6aR)-6-(6-amino-2-{[4'-(trifluoromethyl)biphenyl-3-yl]oxy}-9H-purin-9-yl)tetrahydrofuro[3,4-d][1,3]dioxol-4-yl]methanol; and
((3aR,4R,6R,6aR)-6-{6-amino-2-[3,5-bis(trifluoromethyl)phenyl]-9H-purin-9-yl}tetrahydrofuro[3,4-d][1,3]dioxol-4-yl)methanol.

There are also provided according to the invention methods of synthesis of compound numbers 1-5 as set out in the Examples below. In some cases the precursors of these compounds include one or more protecting groups. It will be appreciated that, if desired, other carboxy-based hydroxyl protecting groups may be used instead of those specified. Synthesis method aspects include:

A process for producing [(3aR,4R,6R,6aR)-6-(6-amino-2-methoxy-9H-purin-9yl)tetrahydrofuro[3,4-d][1,3]dioxol-4-yl]methanol, comprising reacting tribenzoyl-2',3'-methylidene-2-nitro-adenosine with NaOMe and MeOH.

A process for producing [(3aR,4R,6R,6aR)-6-(6-amino-2-(2,2-difluoroethoxy)-9H-purin-9-yl)tetrahydrofuro[3,4-d][1,3]dioxol-4-yl]methanol, comprising reacting tribenzoyl-2',3'-methylidene-2-nitro-adenosine with HOCH$_2$CHF$_2$ and deprotecting the reaction product.

A process for producing [(3aR,4R,6R,6aR)-6-(6-amino-2-(2,5-difluorophenoxy)-9H-purin-9-yl)tetrahydrofuro [3,4-d][1,3]dioxol-4-yl]methanol, comprising reacting tribenzoyl-2',3'-methylidene-2-nitro-adenosine with ArOH, and deprotecting the reaction product, wherein Ar is 2,5-difluorophenyl.

A process for producing [(3aR,4R,6R,6aR)-6-(6-amino-2-{[4'-(trifluoromethyl)-biphenyl-3-yl]oxy}-9H-purin-9-yl)tetrahydrofuro[3,4-d][1,3]dioxol-4-yl]methanol, comprising reacting tribenzoyl-2',3'-methylidene-2-nitro-adenosine with ArOH, and de-protecting the reaction product, wherein Ar is 3-(4-(trifluoromethyl)phenyl)phenyl.

A process for producing ((3aR,4R,6R,6aR)-6-{6-amino-2-[3,5-bis(trifluoromethyl)phenyl]-9H-purin-9yl}tetrahydrofuro[3,4-d][1,3]dioxol-4-yl)methanol, comprising reacting 2',3'-methylidene-2-iodo-adenosine with 3,5-bis(trifluoromethyl)phenylboronic acid.

Prodrugs of the invention are all believed to give rise, in vivo, to active metabolites that have increased affinity for adenosine receptors at pH below pH 7.4. In normal mammalian tissues extracellular pH is tightly regulated between pH 7.35 and 7.45. Some tissues experience lower pH values, particularly the lumen of the stomach (pH between 2 and 3) and the surfaces of some epithelia (for example, the lung surface pH is approximately 6.8). In pathological tissues, for example during inflammation, ischaemia and other types of damage, a reduction in pH occurs.

Because of the increased affinity of the active metabolites (resulting in vivo from the pro-drugs of the invention) for adenosine receptors at reduced pH, it is thought that the actions of these active metabolites can be targeted to regions of low pH, such as pathological tissues. Consequently, the doses of these active metabolites that are required to give therapeutic effects are much lower than would be expected based on their affinity for adenosine receptors at normal extracellular physiological pH. Since only low doses of the active metabolites are required, the serious side effects associated with administration of adenosine receptor agonists, which render them unusable as therapeutic agents, are avoided or minimized.

As described above, the disclosed prodrug compounds can be used for the prevention, treatment, or amelioration of pathological conditions that can be improved or prevented by modulation (agonism or antagonism) of adenosine receptors, such as adenosine A2A receptors. Examples of such pathological conditions include pain, inflammation, and/or arthropathy.

According to the invention there is provided use of a pro-drug of the invention in the manufacture of a medicament for the prevention, treatment, or amelioration of pain, particularly hyperalgesia. There is also provided according to the invention a method of preventing, treating, or ameliorating pain (particularly hyperalgesia) which comprises administering a pro-drug of the invention to a subject in need of such prevention, treatment, or amelioration.

Pro-drugs of the invention are believed to give rise in vivo, to active metabolites that are effective in inhibiting pain perception in mammals suffering from pain, in particular neuropathic or inflammatory pain, even when the pro-drugs are administered at doses expected to give plasma concentrations of the active metabolites well below those known to activate adenosine receptors. Therefore, it is believed that pro-drugs of the invention can treat pain (particularly neuropathic and inflammatory pain) without causing the significant side effects associated with administration of other adenosine receptor agonists.

As mentioned above hyperalgesia is a consequence in most instances of tissue damage, either damage directly to a sensory nerve, or damage of the tissue innervated by a given sensory nerve. Consequently, there are many conditions in which pain perception includes a component of hyperalgesia.

According to the invention there is provided use of a pro-drug of the invention as an analgesic (particularly an anti-hyperalgesic) for the prevention, treatment, or amelioration of pain (particularly hyperalgesia) caused as a result of neuropathy, including Diabetic Neuropathy, Polyneuropathy, Cancer Pain, Fibromyalgia, Myofascial Pain Syndrome, Osteoarthritis, Pancreatic Pain, Pelvic/Perineal pain, Post Herpetic Neuralgia, Rheumatoid Arthritis, Sciatica/Lumbar Radiculopathy, Spinal Stenosis, Temporo-mandibular Joint Disorder, HIV pain, Trigeminal Neuralgia, Chronic Neuropathic Pain, Lower Back Pain, Failed Back Surgery pain, back pain, post-operative pain, post physical trauma pain (including gunshot, road traffic accident, burns), Cardiac pain, Chest pain, Pelvic pain/PID, Joint pain (tendonitis, bursitis, acute arthritis), Neck Pain, Bowel Pain, Phantom Limb Pain, Obstetric Pain (labour/C-Section), Renal Colic, Acute Herpes Zoster Pain, Acute Pancreatitis Breakthrough Pain (Cancer), Dysmenorhoea/Endometriosis; or in any of the above pathological conditions where bacterial or viral infection is a cause or exacerbates the condition.

According to the invention there is also provided use of a pro-drug of the invention as an analgesic (particularly an anti-hyperalgesic) for the prevention, treatment, or amelioration of pain (particularly hyperalgesia) caused as a result of inflammatory disease, or as a result of combined inflammatory, autoimmune and neuropathic tissue damage, including rheumatoid arthritis, osteoarthritis, rheumatoid spondylitis, gouty arthritis, and other arthritic conditions, cancer, HIV, Chronic Obstructive Pulmonary Disease (COPD), acute bronchitis, chronic bronchitis, emphysema, bronchiectasis, cystic fibrosis, pneumonia, pleurisy, acute asthma, chronic asthma, acute respiratory distress syndrome, adult respiratory distress syndrome (ARDS), infant respiratory distress syndrome (IRDS) acute lung injury (ALI), laryngitis, pharangitis, persistent asthma, chronic asthmatic bronchitis, interstitial lung disease, lung malignancies, alpha-anti-trypsin deficiency, bronchiolitis obliterans, sarcoidosis, pulmonary fibrosis, collagen vascular disorders, allergic rhinitis, nasal congestion, status asthmaticus, smoking related pulmonary disease, pulmonary hypertension, pulmonary oedema, pulmonary embolism, pleural effusion, pneumothorax, haemothorax, lung cancer, allergies, pollinosis Hay fever), sneeze, vasomotor rhinitis, mucositis, sinusitis, exogenous irritant induced illness ($SO_2$, smog, pollution), airway hypersensitivity, milk product intolerance, Luffer's pneumonia, pneumoconiosis, collagen induced vascular disease, granulomatous disease, bronchial inflammation, chronic pulmonary inflammatory disease, bone resorption diseases, reperfusion injury (including damage caused to organs as a consequence of reperfusion following ischaemic episodes e.g. myocardial infarcts, strokes), autoimmune damage (including multiple sclerosis, Guillam Barre Syndrome, myasthenia gravis) graft v. host rejection, allograft rejections, fever and myalgia due to infection, AIDS related complex (ARC), keloid formation, scar tissue formation, Crohn's disease, ulcerative colitis and pyresis, irritable bowel syndrome, osteoporosis, cerebral malaria and bacterial meningitis, bowel pain, cancer pain, back pain, fibromyalgia, post-operative pain; or in any of the above pathological conditions where bacterial or viral infection is a cause or exacerbates the condition.

It is believed that pro-drugs of the invention may give rise, in vivo, to active metabolites that are effective in the prevention, treatment, or amelioration of ischaemic pain. The term "ischaemic pain" is used herein to mean pain associated with a reduction in blood supply to a part of the body. A reduced blood supply limits the supply of oxygen (hypoxia) and energy to that part of the body. Ischaemia arises from poor blood perfusion of tissues and so ischaemic pain arises in coronary artery disease, peripheral artery disease, and conditions which are characterized by insufficient blood flow, usually secondary to atherosclerosis. Other vascular disorders can also result in ischaemic pain. These include: left ventricular hypertrophy, coronary artery disease, essential hypertension, acute hypertensive emergency, cardiomyopathy, heart insufficiency, exercise tolerance, chronic heart failure, arrhythmia, cardiac dysrhythmia, syncopy, arteriosclerosis, mild chronic heart failure, angina pectoris, Prinzmetal's (variant) angina, stable angina, and exercise induced angina, cardiac bypass reocclusion, intermittent claudication (arteriosclerosis oblitterens), arteritis, diastolic dysfunction and systolic dysfunction, atherosclerosis, post ischaemia/reperfusion injury, diabetes (both Types I and II), thromboembolisms. Haemorrhagic accidents can also result in ischaemic pain. In addition poor perfusion can result in neuropathic and inflammatory pain arising from hypoxia-induced nerve cell damage (e.g. in cardiac arrest or bypass operation, diabetes or neonatal distress); or in any of the above pathological conditions where bacterial or viral infection is a cause or exacerbates the condition.

Pro-drugs of the invention are believed to give rise, in vivo, to active metabolites that are effective in prevention, treatment, or amelioration of ischaemic pain even when the pro-drugs are administered at doses expected to give plasma concentrations of the active metabolites well below those known to activate adenosine receptors. At these doses, it is believed that the active metabolites do not cause the significant side effects associated with administration of higher doses of adenosine receptor agonists.

There is further provided according to the invention use of a pro-drug of the invention (i.e. a compound of the invention) for the manufacture of a medicament for the prevention, treatment, or amelioration of inflammation. There is further provided according to the invention a method of prevention, treatment, or amelioration of inflammation, which comprises administering a pro-drug of the invention to a subject in need of such prevention, treatment, or amelioration.

In particular, it is believed that pro-drugs of the invention (i.e. compounds of the invention) can be used to prevent, treat, or ameliorate inflammation caused by or associated with: cancer (such as leukemias, lymphomas, carcinomas, colon cancer, breast cancer, lung cancer, pancreatic cancer, hepatocellular carcinoma, kidney cancer, melanoma, hepatic, lung, breast, and prostate metastases, etc.); auto-immune disease (such as organ transplant rejection, lupus erythematosus, graft v. host rejection, allograft rejections, multiple sclerosis, rheumatoid arthritis, type I diabetes mellitus including the destruction of pancreatic islets leading to diabetes and the inflammatory consequences of diabetes); autoimmune damage (including multiple sclerosis, Guillam Barre Syndrome, myasthenia gravis); obesity; cardiovascular conditions associated with poor tissue perfusion and inflammation (such as atheromas, atherosclerosis, stroke, ischaemia-reperfusion injury, claudication, spinal cord injury, congestive heart failure, vasculitis, haemorrhagic shock, vasospasm following subarachnoid haemorrhage, vasospasm following cerebrovascular accident, pleuritis, pericarditis, the cardiovascular complications of diabetes); ischaemia-reperfusion injury, ischaemia and associated inflammation, restenosis following angioplasty and inflammatory aneurysms; epilepsy, neurodegeneration (including Alzheimer's Disease), muscle fatigue or muscle cramp (particularly athletes' cramp), arthritis (such as rheumatoid arthritis, osteoarthritis, rheumatoid spondylitis, gouty arthritis), fibrosis (for example of the lung, skin and liver), multiple sclerosis, sepsis, septic shock, encephalitis, infectious arthritis, Jarisch-Herxheimer reaction, shingles, toxic shock, cerebral malaria, Lyme's disease, endotoxic shock, gram negative shock, haemorrhagic shock, hepatitis (arising both from tissue damage or viral infection), deep vein thrombosis, gout; conditions associated with breathing difficulties (e.g. impeded and obstructed airways, bronchoconstriction, pulmonary vasoconstriction, impeded respiratior, silicosis, pulmonary sarcosis, pulmonary hypertension, pulmonary vasoconstriction, bronchial allergy and vernal conjunctivitis); conditions associated with inflammation of the skin (including psoriasis, eczema, ulcers, contact dermatitis); conditions associated with inflammation of the bowel (including Crohn's disease, ulcerative colitis and pyresis, irritable bowel syndrome, inflammatory bowel disease); HIV (particularly HIV infection), cerebral malaria, bacterial meningitis, TNF-enhanced HIV replication, TNF inhibition of AZT and DDI activity, osteoporosis and other bone resorption diseases, osteoarthritis, rheumatoid arthritis, infertility from endometriosis, fever and myalgia due to infection, cachexia secondary to cancer, cachexia secondary to infection or malignancy, cachexia secondary to acquired immune deficiency syndrome (AIDS), AIDS related complex (ARC), keloid formation, scar tissue formation, adverse effects from amphotericin B treatment, adverse effects from interleukin-2 treatment, adverse effects from OKT3 treatment, or adverse effects from GM-CSF treatment, and other conditions mediated by excessive anti-inflammatory cell (including neutrophil, eosinophil, macrophage and T-cell) activity; or in any of the above pathological conditions where bacterial or viral infection is a cause or exacerbates the condition.

Continuous low grade inflammation is known to be associated with obesity (in the presence and absence of insulin resistance and Type II diabetes) (Browning et al Metabolism (2004) 53, 899-903, Inflammatory markers elevated in blood of obese women; Mangge et al, Exp Clin Endocrinol Diabetes (2004) 112, 378-382, Juvenile obesity correlates with serum inflammatory marker C-reactive protein; Maachi et al Int J Obes Relat Metab Disord. (2004) 28, 993-997, Systemic low grade inflammation in obese people). A possible reason for this is that fat cells secrete TNF alpha and interleukins 1 and 6, which are pro-inflammatory.

Pro-drugs of the invention that give rise, in vivo, to active metabolites that are selective agonists of adenosine A2A and/or A3 receptors are particularly preferred because it is believed that such metabolites will have strong anti-inflammatory activity. By selective agonists of adenosine A2A and/or A3 receptors is meant agonists that activate adenosine A2A and/or A3 receptors at concentrations that are lower (preferably one thousandth to one fifth) than required to activate adenosine A1 receptors. Furthermore, A1 receptors have pro-inflammatory activity, so such effects are expected to be minimized for compounds that are selective for A2A and/or A3 receptors.

It will be appreciated that any pathological condition that can be prevented or improved by agonism of adenosine A2A and/or A3 receptors can be prevented, treated, or ameliorated by pro-drugs of the invention.

According to the invention there is provided use of a pro-drug of the invention in the manufacture of a medicament for the prevention, treatment, or amelioration of a pathological condition that can be improved or prevented by agonism of adenosine A2A and/or A3 receptors. There is also provided according to the invention a method of prevention, treatment, or amelioration of a pathological condition that can be improved or prevented by agonism of adenosine A2A and/or A3 receptors, which comprises administering a pro-drug of the invention to a subject in need of such prevention, treatment, or amelioration.

A person of ordinary skill in the art can readily test whether or not a pathological condition that is prevented, treated, or ameliorated by a compound of the invention is acting via adensoine A2A and/or A3 receptors. For example, this may be done by comparing the effect of the compound in an animal model of the pathological condition in the presence and absence of a selective antagonist of an adenosine A2A and/or A3 receptor. If the effect of the compound in the presence of the antagonist is reduced or absent compared with the effect of the compound in the absence of the antagonist, it is concluded that the compound is exerting its effect via an adenosine A2A and/or A3 receptor. Antagonists of adenosine A2A and A3 receptors are known to those of ordinary skill in the art (see for example Ongini et al., Farmaco. (2001) January-February, 56(1-2), 87-90; Muller, Curr Top Med. Chem. (2003) 3(4), 445-62).

Alternatively, an adenosine A2A receptor knockout mouse may be used (Ohta A and Sitkovsky M, Nature (2001) 414, 916-20). For example, the effect of the compound on a mouse that has symptoms of the pathological condition is compared with its effect on an adenosine A2A knockout mouse that has corresponding symptoms. If the compound is only effective in the mouse that has adenosine A2A receptors it is concluded that the compound is exerting its effect via adenosine A2A receptors.

Pro-drugs of the invention are believed give rise, in vivo, to active metabolites that are much more effective at low doses than other adenosine receptor agonists. Thus, it is expected that pro-drugs of the invention can be effectively administered at doses at which they have reduced probability and severity of side effects, or at which side effects are not observed. Such compounds provide significant advantages over the vast majority of other adenosine receptor agonists which only have anti-inflammatory effects at the same concentrations at which serious side effects are observed.

Compounds of the invention may alternatively or additionally have reduced probability and severity of side effects compared to other adenosine receptor agonists.

It is also believed that pro-drugs of the invention may be effective as disease-modifying anti-rheumatic drugs (DMARDs), in particular for use in the prevention, treatment, or amelioration of rheumatoid arthritis, and possibly other arthropathies such as osteoarthritis.

Medications used to treat rheumatoid arthritis (RA) can be divided into two groups: those that help relieve RA symptoms; and those that help modify the disease. Drugs that help to relieve RA symptoms include nonsteroidal anti-inflammatory drugs (NSAIDs) that relieve pain and reduce inflammation in the affected joints, analgesics (such as acetaminophen and narcotic pain medications) that relieve pain but do not slow joint damage or reduce inflammation, and corticosteroids that are anti-inflammatory drugs.

DMARDs help to improve RA symptoms (such as joint swelling and tenderness), but also slow the progression of joint damage caused by RA. Thus, while there is no cure for RA, DMARDs help to slow the progression of RA. In the past DMARDs were usually used to treat RA after NSAID therapy failed. However, DMARDs are now beginning to be used earlier in the course of RA because studies have suggested that early intervention with DMARDs offers important benefits. DMARDs and NSAIDs are often used in combination with each other.

Results from clinical studies have shown that known DMARDs slow the progression of RA. After 6 months of treatment, the rate of bone and cartilage damage had already started to slow in patients' joints. After 1 year, patients showed very little progression of joint damage, and after 2 years X rays showed that few patients in the study had newly damaged joints during the second year of treatment.

Examples of known DMARDs include sulphasalazine, penicillamine, chloroquine, hydroxychloroquine, gold (by intranuscular injection or orally as auranofin), methotrexate, cyclosporin, azathioprine, cyclophosphamide, leflunomide. More recently biological DMARDs have been developed which inhibit tumour necrosis factor alpha (TNF alpha). One example is Humira® which is indicated for reducing signs and symptoms and inhibiting the progression of structural damage in adults with moderately to severely active RA who have had an inadequate response to one or more DMARDs. Humira® is an anti-TNF alpha antibody.

Many of the known DMARDs cause serious side effects. Consequently, it is desired to provide new DMARDs that can be administered with minimal side effects.

WO 2005/084653 shows the ability of spongosine to reduce phorbol ester induced TNF alpha release in U937 human macrophage cells. On this basis, it is believed that spongosine and related compounds of the invention also have DMARD activity.

According to the invention there is provided use of a pro-drug of the invention in the manufacture of a medicament for slowing the progression of arthropathy. There is also provided according to the invention a method of slowing the progression of arthropathy, which comprises administering a pro-drug of the invention to a subject in need thereof.

Preferably the progression of RA is slowed, and in particular the progression of joint damage caused by RA. A compound of the invention may be administered to the subject at any stage in the course of RA. A compound of the invention may be administered in combination with one or more NSAIDs or other DMARDs.

Pro-drugs of the invention are believed to give rise, in vivo, to active metabolites that are effective as DMARDs even when the pro-drugs are administered at doses expected to give plasma concentrations of the active metabolites well below those known to activate adenosine receptors. At these doses, it is believed that the active metabolites do not cause the significant side effects associated with administration of higher doses of spongosine, or other adenosine receptor agonists.

A particular advantage of use of pro-drugs of the invention as DMARDs is that it is believed that they will be orally active, in contrast to anti-TNF alpha antibodies which must be injected.

It has also been appreciated that pro-drugs of the invention may give rise, in vivo, to active metabolites that may be effective in preventing, treating, or ameliorating macro and micro vascular complications of type 1 or 2 diabetes (including retinopathy, nephropathy, autonomic neuropathy), or blood vessel damage caused by ischaemia (either diabetic or otherwise) or atherosclerosis (either diabetic or otherwise).

According to the invention, there is provided use of a pro-drug of the invention in the manufacture of a medicament for the prevention, treatment, or amelioration of macro or micro vascular complications of type 1 or 2 diabetes, retinopathy, nephropathy, autonomic neuropathy, or blood vessel damage caused by ischaemia or atherosclerosis. According to the invention there is also provided a method of preventing, treating, or ameliorating macro or micro vascular complications of type 1 or 2 diabetes, retinopathy, nephropathy, autonomic neuropathy, or blood vessel damage caused by ischaemia or atherosclerosis, in a subject in need of such prevention, treatment, or amelioration, which comprises administering a pro-drug of the invention to the subject.

Pro-drugs of the invention are believed to be effective in prevention, treatment, or amelioration of macro or micro vascular complications of type 1 and 2 diabetes, including retinopathy, nephropathy, autonomic neuropathy, or blood vessel damage caused by ischaemia or atherosclerosis (either diabetic or otherwise)) even when the pro-drugs are administered at doses expected to give plasma concentrations of the active metabolites resulting in vivo, well below those known to activate adenosine receptors. At these doses, it is believed that the compounds do not cause the significant side effects associated with administration of higher doses of adenosine receptor agonists.

Pro-drugs of the invention are also believed to be effective in the promotion of wound healing. According to the invention there is provided use of a pro-drug of the invention in the manufacture of a medicament for the promotion of wound healing. There is also provided according to the invention a method of promoting wound healing in a subject, which comprises administering a pro-drug of the invention to the subject.

The amount of a pro-drug of the invention that is administered to a subject is preferably an amount which gives rise to a peak plasma concentration of the active metabolite resulting in vivo, that is less than the $EC_{50}$ value of the compound at adenosine receptors (preferably at pH 7.4).

It will be appreciated that the $EC_{50}$ value of the active metabolite is likely to be different for different adenosine receptors (i.e. the A1, A2A, A2B, A3 adenosine receptors). The amount of the pro-drug that is to be administered should be calculated relative to the lowest $EC_{50}$ value of the active metabolite at the different receptors.

Thus, preferably the amount of a pro-drug of the invention that is administered to a subject should be an amount which gives rise to a peak plasma concentration of the active metabolite resulting in vivo, that is less than the lowest $EC_{50}$ value of the active metabolite at adenosine receptors.

Preferably the peak plasma concentration of the active metabolite resulting in vivo following dosing of the pro-drug, is one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one third, or one fiftieth to one half, or one fiftieth to one fifth, or one tenth to one half, or one tenth to one fifth) of the lowest $EC_{50}$ value.

Preferably the amount of a pro-drug of the invention that is administered gives rise to a plasma concentration of the active metabolite resulting in vivo, that is maintained for more than one hour at one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one fifth, or one tenth to one half, or one tenth to one fifth) of the lowest $EC_{50}$ value of the active metabolite at adenosine receptors.

Preferably the amount of the pro-drug administered gives rise to a plasma concentration of the active metabolite resulting in vivo that is maintained for more than one hour between one thousandth and one half, or one thousandth and one fifth, or one thousandth and one twentieth, or one hundredth and one half, or one hundredth and one fifth, or one fiftieth and one half, or one fiftieth and one fifth, of the $EC_{50}$ value of the active metabolite at adenosine receptors at pH 7.4.

For the avoidance of doubt, the $EC_{50}$ value of a compound is defined herein as the concentration of the compound that provokes a receptor response halfway between the baseline receptor response and the maximum receptor response (as determined, for example, using a dose-response curve).

The $EC_{50}$ value should be determined under standard conditions (balanced salt solutions buffered to pH 7.4). For $EC_{50}$ determinations using isolated membranes, cells and tissues this would be in buffered salt solution at pH 7.4 (e.g. cell culture medium), for example as in Daly et al., Pharmacol. (1993) 46, 91-100), or preferably as in Tilburg et al (J. Med. Chem. (2002) 45, 91-100). The $EC_{50}$ could also be determined in vivo by measuring adenosine receptor mediated responses in a normal healthy animal, or even in a tissue perfused under normal conditions (i.e. oxygenated blood, or oxygenated isotonic media, also buffered at pH 7.4) in a normal healthy animal.

Alternatively, the amount of a pro-drug of the invention that is administered may be an amount that results in a peak plasma concentration of the active metabolite resulting in vivo, that is less than the lowest or highest $K_d$ value of the compound at adenosine receptors (i.e. less than the lowest or highest $K_d$ value of the compound at A1, A2A, A2B, and A3 adenosine receptors). Preferably the peak plasma concentration of the active metabolite, is one ten thousandth to one half (or one ten thousandth to one fifth, or one ten thousandth to one twentieth, or one ten thousandth to one hundredth, or one ten thousandth to one thousandth, or one thousandth to one half, or one thousandth to one third, or one thousandth to one fifth, or one thousandth to one twentieth, or one fiftieth to one tenth, or one hundredth to one half, or one hundredth to one fifth, or one fiftieth to one half, or one fiftieth to one fifth, or one tenth to one half, or one tenth to one fifth) of the lowest or highest $K_d$ value.

Preferably the amount of the pro-drug that is administered is an amount that results in a plasma concentration of the active metabolite resulting in vivo, that is maintained for at least one hour between one thousandth and one half, or one thousandth and one fifth, more preferably between one thousandth and one twentieth, or one hundredth and one half, or one hundredth and one fifth, or one fiftieth and one half, or one fiftieth and one fifth, of the $K_d$ value of the active metabolite at adenosine receptors.

Preferably the amount of the pro-drug that is administered is an amount that results in a plasma concentration of the active metabolite resulting in vivo, that is maintained for more than one hour at one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one fifth, or one fiftieth to one third, or one tenth to one half, or one tenth to one fifth) of the lowest or highest $K_d$ value of the active metabolite at adenosine receptors.

The $K_d$ value of the active metabolite, resulting in vivo following administration of the pro-drug, at each receptor should be determined under standard conditions using plasma membranes as a source of the adenosine receptors derived either from tissues or cells endogenously expressing these receptors or from cells transfected with DNA vectors encoding the adenosine receptor genes. Alternatively whole cell preparations using cells expressing adenosine receptors can be used. Labeled ligands (e.g. radiolabeled) selective for the different receptors should be used in buffered (pH 7.4) salt solutions (see e.g. Tilburg et al, J. Med. Chem. (2002) 45, 420-429) to determine the binding affinity and thus the $K_d$ of the active metabolite at each receptor.

Alternatively, the amount of a pro-drug of the invention that is administered may be an amount that is one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one third, or one fiftieth to one fifth, or one tenth to one half, or one tenth to one fifth) of the minimum amount (or dose) of the pro-drug that gives rise to bradycardia, hypotension or tachycardia side effects in animals of the same species as the subject to which the compound is to be administered. Preferably the amount of the pro-drug administered gives rise to a plasma concentration of the active metabolite resulting in vivo, that is maintained for more than one hour at one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one fifth, or one tenth to one half, or one tenth to one fifth) of the minimum amount of the active metabolite that gives rise to the side effects.

Preferably the amount of the pro-drug administered gives rise to a plasma concentration of the active metabolite resulting in vivo, that is maintained for more than 1 hour between one thousandth and one half, or one thousandth and one twentieth, or one hundredth or one fiftieth and one half, or one hundredth or one fiftieth and one fifth of the minimum dose that gives rise to the side effects.

Alternatively, the amount of a pro-drug of the invention that is administered may be an amount that gives rise to a plasma concentration of the active metabolite resulting in vivo, that is one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one third, or one fiftieth to one fifth, or one tenth to one half, or one tenth to one fifth) of the minimum plasma concentration of the active metabolite that causes bradycardia, hypotension or tachycardia side effects in animals of the same species as the subject to which the compound is to be administered. Preferably the amount of the pro-drug administered gives rise to a plasma concentration of the active metabolite, that is maintained for more than one hour at one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one fifth, or one tenth to one half, or one tenth to one fifth) of the minimum plasma concentration of the active metabolite that causes the side effects.

Preferably the amount of the pro-drug administered gives rise to a plasma concentration of the active metabolite resulting in vivo, that is maintained for more than 1 hour between one thousandth and one half, or one thousandth and one twentieth, or one hundredth or one fiftieth and one half, or one hundredth or one fiftieth and one fifth, of the minimum plasma concentration that causes the side effects.

The appropriate dosage of a pro-drug of the invention will vary with the age, sex, weight, and condition of the subject being treated, the potency of the pro-drug and/or the active metabolite resulting in vivo following dosing of the pro-drug, (such as their $EC_{50}$ values for an adenosine receptor), the half life of the pro-drug and/or the active metabolite, its absorption by the body, and the route of administration, etc. However, the appropriate dosage can readily be determined by one skilled in the art.

A suitable way to determine the appropriate dosage is to assess cardiovascular changes (for example by ECG and blood pressure monitoring) at or around the $EC_{50}$ value of the pro-drug and/or the active metabolite (resulting in vivo following dosing of the pro-drug), for an adenosine receptor (preferably the receptor for which it/they has/have highest affinity) to determine the maximum tolerated dose. The therapeutically effective dose is then expected to be one ten thousandth to one half (or one ten thousandth to one fifth, or one ten thousandth to one twentieth, or one ten thousandth to one hundredth, or one ten thousandth to one thousandth, or one thousandth to one half, or one thousandth to one fifth, or one thousandth to one twentieth, or one fiftieth to one tenth, or one hundredth to one half, or one hundredth to one fifth, or one fiftieth to one half, or one fiftieth to one third, or one fiftieth to one fifth, or one tenth to one half, or one tenth to one fifth) of the maximum tolerated dose.

WO 2005/084653 shows that for spongosine the dose should be less than 28 mg in humans. This dose gives rise to plasma concentrations between 0.5 and 0.9 µM (close to the $K_d$ at adenosine A2A receptors at pH 7.4 see below). Based on this result, the preferred dosage range for spongosine is 0.03 to 0.3 mg/kg. The preferred dosage range of the pro-drugs of the invention is 0.03 to 8 mg/kg.

The minimum plasma concentration of spongosine giving maximal analgesic relief in a rat adjuvant model of arthritis was 0.06 µM, considerably less than the $EC_{50}$ of spongosine at the adenosine A2A receptor which is approximately 1 µM. The preferred dosing levels in humans give maximum plasma concentrations between 0.005 and 0.5 µM which are significantly lower than those expected to give an analgesic or an anti-inflammatory effect by an action on this receptor.

Alternatively, appropriate therapeutic concentrations of the active metabolites (resulting, in vivo, following dosing of the pro-drugs of the invention) are expected to be approximately 10-20 times the $K_i$ for an adenosine receptor (the receptor for which the active metabolite has the highest affinity) at pH 5.5. Thus, for spongosine 15 to 30 nM is required whereas using the $K_i$ at pH7.4 the concentration that is expected to be required is 20 to 30 µM.

It is expected that the amount of a pro-drug of the invention that is administered should be 0.001-15 mg/kg. The amount may be less than 6 mg/kg. The amount may be at least 0.001, 0.01, 0.1, or 0.2 mg/kg. The amount may be less than 0.1, or 0.01 mg/kg. Preferred ranges are 0.001-10, 0.001-5, 0.001-2, 0.001-1, 0.001-0.1, 0.001-0.01, 0.01-15, 0.01-10, 0.01-5, 0.01-2, 0.01-1, 0.1-10, 0.1-5, 0.1-2, 0.1-1, 0.1-0.5, 0.1-0.4, 0.2-15, 0.2-10, 0.2-5, 0.2-2, 0.2-1.2, 0.2-1, 0.6-1.2, mg/kg.

Preferred doses for a human subject (for example a 70 kg subject) are less than 420 mg, preferably less than 28 mg, more preferably less than 21 mg, and preferably at least 0.07, 0.1, 0.7, or 0.8 mg, more preferably at least 3.5 or 7 mg. More preferably 7-70 mg, 14-70 mg, or 3.5-21 mg.

It is believed that the dosage amounts specified above are significantly lower (up to approximately 5000 times lower) than would be expected to be required for an analgesic or an anti-inflammatory effect based on the $EC_{50}$ value of the compound at the adenosine A2A receptor.

The preferred dosage amounts specified above are aimed at producing plasma concentrations of active metabolites (resulting, in vivo, following dosing of the pro-drugs of the invention), that are approximately one hundredth to one half of the $EC_{50}$ value of the active metabolite at the adenosine receptor for which it has highest affinity.

A pro-drug of the invention may be administered with or without other therapeutic agents, for example analgesics or anti-inflammatories (such as opiates, steroids, NSAIDs, cannabinoids, tachykinin modulators, or bradykinin modulators) or anti-hyperalgesics (such as gabapentin, pregabalin, cannabinoids, sodium or calcium channel modulators, anti-epileptics or anti-depressants), or DMARDs.

In general, a pro-drug of the invention may be administered by known means, in any suitable formulation, by any suitable route. A pro-drug of the invention is preferably administered orally, parenterally, sublingually, transdermally, intrathecally, or transmucosally. Other suitable routes include intravenous, intramuscular, subcutaneous, inhaled, and topical. The amount of drug administered will typically be higher when administered orally than when administered, say, intravenously.

It will be appreciated that a pro-drug of the invention may be administered together with a physiologically acceptable carrier, excipient, or diluent.

To maintain therapeutically effective plasma concentrations for extended periods of time, pro-drugs of the invention may be incorporated into slow release formulations.

Suitable compositions, for example for oral administration, include solid unit dose forms, and those containing liquid, e.g. for injection, such as tablets, capsules, vials and ampoules, in which the active agent is formulated, by known means, with a physiologically acceptable excipient, diluent or carrier. Suitable diluents and carriers are known, and include, for example, lactose and talc, together with appropriate binding agents etc.

A unit dosage of a pro-drug of the invention typically comprises up to 500 mg (for example 1 to 500 mg, or (preferably) 5 to 500 mg) of the active agent (pro-drug). Preferably the active agent is in the form of a pharmaceutical composition comprising the active agent and a physiologically acceptable carrier, excipient, or diluent. Preferred dosage ranges (i.e. preferred amounts of the active ingredient in a unit dose) are 0.001-10, 0.001-5, 0.001-2, 0.001-1, 0.001-0.1, 0.001-0.01, 0.01-15, 0.01-10, 0.01-5, 0.01-2, 0.01-1, 0.1-10, 0.1-5, 0.1-2, 0.1-1, 0.1-0.5, 0.1-0.4, 0.2-15, 0.2-10, 0.2-5, 0.2-2, 0.2-1.2, 0.2-1, 0.5 to 1, 0.6-1.2, typically about 0.2 or 0.6, mg of the active agent per kg of the (human) subject. Preferred amounts of the active agent are less than 420 mg, preferably less than 28 mg, more preferably less than 21 mg, and preferably at least 0.07, 0.1, 0.7 or 0.8 mg, more preferably at least 3.5 or 7 mg. More preferably 7 to 70 mg, or 14 to 70 mg, 3.5 to 21 mg, 0.07-0.7 mg, or 0.7-7 mg. At these levels, it is believed that effective treatment can be achieved substantially without a concomitant fall (for example, no more than 10%) in blood pressure and/or increase in compensatory heart rate.

A unit dosage of a pro-drug of the invention may further comprise one or more other therapeutic agents, for example analgesics, anti-inflammatories, anti-hyperalgesics, or DMARDs.

Preferably a pro-drug of the invention is administered at a frequency of 2 or 3 times per day.

Pro-drugs of the invention can also serve as a basis for identifying more effective drugs, or drugs that have further reduced side effects.

The following definitions shall apply throughout the specification and the appended claims.

The term "$C_{1-6}$-alkyl" denotes a straight or branched alkyl group having from 1 to 6 carbon atoms. Examples of said lower alkyl include methyl, ethyl, n-propyl, iso-propyl, n-butyl, iso-butyl, sec-butyl, t-butyl and straight- and branched-chain pentyl and hexyl. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc.

The term "$C_{3-8}$-cycloalkyl" denotes a cyclic alkyl group having a ring size from 3 to 8 carbon atoms. Examples of said cycloalkyl include cyclopropyl, cyclobutyl, cyclopentyl, cyclohexyl, methylcyclohexyl, cycloheptyl, and cyclooctyl. For parts of the range "$C_{3-8}$-cycloalkyl" all subgroups thereof are contemplated such as $C_{3-7}$-cycloalkyl, $C_{3-6}$-cycloalkyl, $C_{3-5}$-cycloalkyl, $C_{3-4}$-cycloalkyl, $C_{4-8}$-cycloalkyl, $C_{4-7}$-cycloalkyl, $C_{4-6}$-cycloalkyl, $C_{4-5}$-cycloalkyl, $C_{5-7}$-cycloalkyl, $C_{6-7}$-cycloalkyl, etc.

The term "halogen" shall mean fluorine, chlorine, bromine or iodine.

The term "aryl" refers to a hydrocarbon ring system having at least one aromatic ring. Examples of aryls are phenyl, pentalenyl, indenyl, indanyl, isoindolinyl, chromanyl, naphthyl, fluorenyl, anthryl, phenanthryl and pyrenyl. The aryl rings may optionally be substituted with $C_{1-6}$-alkyl. Examples of substituted aryl groups are 2-methylphenyl and 3-methylphenyl.

The term "heteroaryl" means in the present description a monocyclic, bi- or tricyclic aromatic ring System (only one ring need to be aromatic) having from 5 to 14, preferably 5 to 10 ring atoms such as 5, 6, 7, 8, 9 or 10 ring atoms (mono- or bicyclic), in which one or more of the ring atoms are other than carbon, such as nitrogen, sulfur, oxygen and selenium as part of the ring System. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, chroman, isochroman, quinoline, quinoxaline, isoquinoline, phthalazine, cinnoline, quinazoline, indole, isoindole, indoline (i e 2,3-dihydroindole), isoindoline (i e 1,3-dihydroisoindole), benzothiophene, benzofuran, 2,3-dihydrobenzofuran, isobenzofuran, benzodioxole, benzothiadiazole, benzotriazole, benzoxazole, 2,1,3-benzoxadiazole, benzopyrazole, 2,1,3-benzothiazole, 2,1,3-benzoselenadiazole, benzimidazole, indazole, benzodioxane, 2,3-dihydro-1,4-benzodioxine, indane, 1,2,3,4-tetrahydroquinoline, 3,4-dihydro-2H-1,4-benzoxazine, 1,5-naphthyridine, 1,8-naphthyridine, pyrido[3,2-b]thiophene, acridine, fenazine and xanthene.

The term "heterocyclic" and "heterocyclyl" in the present description is intended to include unsaturated as well as partially and fully saturated mono-, bi- and tricyclic rings having from 4 to 14, preferably 4 to 10 ring atoms having one or more heteroatoms (e.g., oxygen, sulfur, or nitrogen) as part of the ring System and the reminder being carbon, such as, for example, the heteroaryl groups mentioned above as well as the corresponding partially saturated or fully saturated heterocyclic rings. Exemplary saturated heterocyclic rings are azetidine, pyrrolidine, piperidine, piperazine, morpholine, thiomorpholine, 1,4-oxazepane, azepane, phthalimide, indoline, isoindoline, 1,2,3,4-tetrahydroquinoline, 1,2,3,4-tetrahydroisoquinoline, hexahydroazepine, 3,4-dihydro-2(1H) isoquinoline, 2,3-dihydro-1H-indole, 1,3-dihydro-2H-isoindole, azocane, 1-oxa-4-azaspiro[4.5]dec-4-ene, decahydroisoquinoline, 1,2-dihydroquinoline, and 1,4-diazepane.

The term 'methylidene acetal' in the present description is intended to denote an acetal of structure $ROCH_2OR'$ "Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

The term "prodrug forms" means a pharmacologically acceptable derivative, such as an ester or an amide, which derivative is biotransformed in the body to form the active drug. Reference is made to Goodman and Gilman's, The Pharmacological basis of Therapeutics, 8$^{th}$ ed., Mc-Graw-Hill, Int. Ed. 1992, "Biotransformation of Drugs", p. 13-15.

The term "active metabolite" means the pharmacologically active compound released following metabolism of the prodrug in-vivo.

The following abbreviations have been used:
Aq Aqueous
Ar Aryl
Bz Benzoyl
DCM Dichloromethane
DMARD Disease modifying antirheumatic drug
EC50 50% Effective concentration
EDTA ethylenediaminetetraacetic acid
ES$^+$ Electrospray
EtOAc Ethyl acetate
HIV Human immunodeficiency virus
HPLC High performance liquid chromatography
IV Intravenous
JV Jugular vein
Kd Dissociation constant
LCMS Liquid chromatography mass spectrometry
M Molar
[MH$^+$] Protonated molecular ion
RP Reverse phase
Me Methyl
MS Mass spectrometry
NSAID Non steroidal anti-inflammatory drug
PK Pharmacokinetic
PO Per oral
PSA Polar surface area
RA Rheumatoid arthritis
SD Sprague Dawley
THF Tetrahydrofuran
TMAN Tetramethylammonium nitrate
TFA Trifluoroacetic acid
TFAA Trifluoroacetic anhydride All isomeric forms possible (pure enantiomers, diastereomers, tautomers, racemic mixtures and unequal mixtures of two enantiomers) for the compounds delineated within the scope of the invention. Such compounds can also occur as cis- or trans-, E- or Z-double bond isomer forms. All isomeric forms are contemplated.

The compounds of Formula (I) may be used as such or, where appropriate, as pharmacologically acceptable salts (acid or base addition salts) thereof. The pharmacologically acceptable addition salts mentioned above are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulfuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulfonic acid, toluenesulfonic acid, methanesulfonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

For clinical use, the compounds of the invention are formulated into pharmaceutical formulations for oral, rectal, parenteral or other mode of administration. Pharmaceutical formulations are usually prepared by mixing the active substance, or a pharmaceutically acceptable salt thereof, with conventional pharmaceutical excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

In a further aspect the invention relates to methods of making compounds of any of the formulae herein comprising reacting any one or more of the compounds of the formulae delineated herein, including any processes delineated herein. The compounds of Formula (I) above may be prepared by, or in analogy with, conventional methods.

The processes described above may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are mentioned above.

The compounds of Formula (I) may possess one or more chiral carbon atoms, and they may therefore be obtained in the form of optical isomers, e.g., as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes delineated herein may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The necessary starting materials for preparing the compounds of Formula (I) are either known or may be prepared in analogy with the preparation of known compounds.

Figure 1:
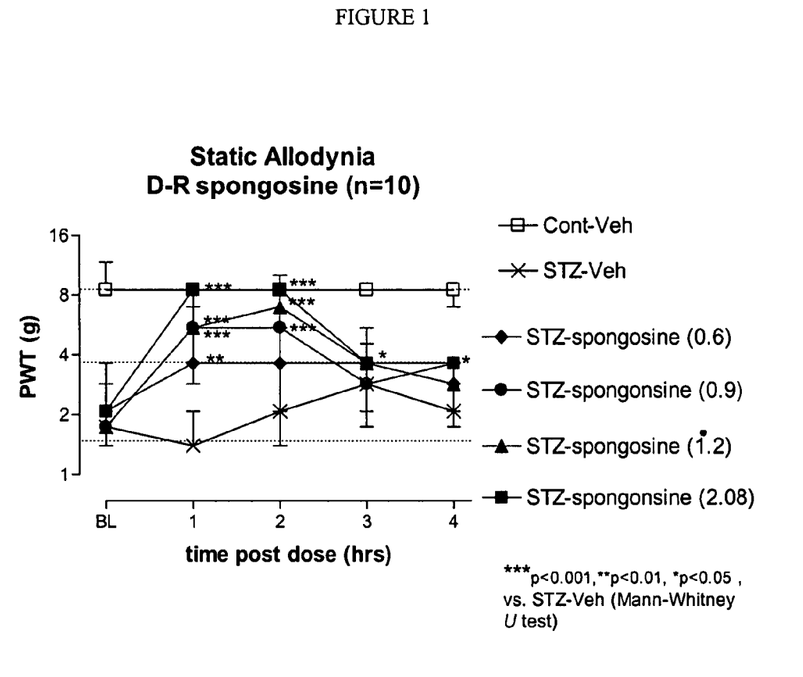
FIG. 1 shows that spongosine exhibited dose dependant effects (0.6-2.1 mg/kg, po) on the reversal of streptozocin induced static allodynia. All doses were effective at reversing allodynia, whilst the top dose fully reversed the allodynia to levels exhibited by naïve non-streptozocin injected control animals. Static allodynia was assessed using von Frey hairs and the paw withdrawal threshold (PWT) in grams (symbols represent the median and vertical bars represent the first and third quartiles) is indicated. All doses of spongosine tested alleviated static allodynia resulting in an increase in the PWT i.e. in the ability of the animal to withstand increased pressure exerted by the von Frey hairs. **$p<0.01$, *$p<0.05$ significantly different (Mann-Whitney U test) comparing drug treated STZ group to vehicle treated STZ group at each time point. Significant alleviation of allodynia was still evident in the 2.1 mg/kg dose cohort at 2, 3 and 4 hours.

Embodiments of the invention are described in the following examples with reference to the accompanying drawing in which:

FIG. 1 shows the effect of spongosine on the maintenance of streptozocin (STZ)-induced diabetic neuropathy as measured by static allodynia.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The specific examples below are to be construed as merely illustrative, and not limitative of the remainder of the disclosure many way whatsoever. Without further elaboration, it is believed that one skilled in the art can, based on the description herein, utilize the present invention to its fullest extent. All publications cited herein are hereby incorporated by reference in their entirety.

Experimental Methods

All reagents were commercial grade and were used as received without further purification, unless otherwise specified. Reagent grade solvents were used in all cases. The 2-iodo adenosine was supplied by General Intermediates of Canada, Inc Electrospray mass spectrometry (MS) was obtained using a waters ZQ mass spectrometer. Analytical HPLC were performed on Agilent 1100 system equipped with Phenomenex Synergi Hydro RP (C18, 150×4.6 mm) using the eluent system: water/0.1% TFA and $CH_3CN$, 1.5 mL/min, with a gradient time of 7 min for both HPLC and LC-MS.

EXAMPLES

Example 1

Preparation of [(3aR,4R,6R,6aR)-6-(6-amino-2-methoxy-9H-purin-9yl)tetrahydrofuro[3,4-d][1,3]dioxol-4-yl]methanol 10

Scheme 1

To a suspension of adenosine (20 g, 74.9 mmol) in DMF (100 mL) was added imidazole (5.08 g, 74.9 mmol) and TBDMSCl (11.3 g, 74.9 mmol) and the resulting suspension stirred for 2 h before being quenched with sat. aq. NaHCO$_3$. The crude reaction mixture was then extracted into ethyl acetate and the organic fraction was washed with brine and water (×3) and dried over MgSO$_4$. The solution was then concentrated to approximately 500 mL and allowed to stand for 1 h. The resulting white precipitate was filtered and washed with ethyl acetate to yield 28 in 2 batches as a white solid (14.07 g, 49%).

A solution of NaOH (50 g, 1.25 mol) in water (100 mL) was added drop-wise to a solution of dibromomethane (30 mL, 0.43 mol), 28 (11.8 g, 30.9 mmol) and tetrabutylammonium bromide (200 mg, cat.) in DCM (300 mL) and the resulting solution heated at 40° C. for 72 h. The organic layer was then separated and washed with water (×5) and dried over MgSO$_4$ to yield 29 which was used without further purification.

To a solution of 29 (assume 30.9 mmol) in THF (300 mL) was added tetrabutylammonium fluoride (TBAF) (30.9 mL, 1M solution in THF, 30.9 mmol) and stirring continued for 1 h before addition of aq. NH$_4$Cl (10 mL) and concentration in vacuo to afford crude 30 which was used without purification.

To a solution of 30 (assume 30.9 mmol) in pyridine (75 mL) was added benzoyl chloride (13.9 mL, 120 mmol) and the resulting solution was refluxed at 80° C. for 4 h. Further benzoyl chloride (5 mL, 10 mL and 10 mL) was added after 4 h, 8 h and 16 h respectively and heating was continued for 24 h. The solvents were removed in vacuo and the residue dissolved in EtOAc and washed with aq. NH$_4$Cl, aq. NaHCO$_3$ and brine, and the organic phase dried over MgSO$_4$. Purification by flash column chromatography (normal phase, ICN silica, 18-32µ, gradient 10-67% EtOAc in heptane, residue dry loaded) afforded 31 as a white solid (12.1 g, 66% over 3 steps).

To a suspension of TMAN (3.70 g, 30.7 mmol) in DCM (150 mL) was added TFAA (4.40 mL, 30.7 mmol) and the resulting suspension cooled to 0° C. before the drop-wise addition of a solution of 31 (12.1 g, 20.5 mmol) in DCM (150 mL). The reaction mixture was stirred at 0° C. for 6 h and was then allowed to warm to room temperature over 16 h. The solvents were removed in vacuo and the residue dissolved in EtOAc (150 mL) and washed with water (100 mL×3) and brine (100 mL), and the organic phase dried over MgSO$_4$. Trituration from DCM/ethanol afforded 32 as a yellow foam (9.8 g, 75%) which was used without further purification.

To a solution of 32 (2 g, 3.14 mmol) in methanol (50 mL) was added NaOMe (1.04 g, 19.3 mmol) and the resulting solution stirred at room temperature for 16 h. Silica gel (10 g) was then added and the solvents removed in vacuo. Purification by flash column chromatography (normal phase, ICN silica, 18-32, gradient 5-20% ethanol in DCM, residue dry loaded) and recrystallisation from hot water afforded [(3aR, 4R,6R,6aR)-6-(6-amino-2-methoxy-9H-purin-9-yl)tetrahydrofuro[3,4-d][1,3]dioxol-4-yl]methanol 10 as colourless needles (209 mg, 22%).

HPLC (Phenomenex® Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 3.88 min, 100%.

LCMS (Phenomenex® Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 4.44 min, 100%, ES$^+$: 360.389 [MH]$^+$.

Example 2

Preparation of [(3aR,4R,6R,6aR)-6-(6-amino-2-(2,2-difluoroethoxy)-9H-purin-9-yl)-tetrahydrofuro[3,4-d][1,3]dioxol-4-yl]methanol 11

Scheme 2

To a solution of CHF$_2$CH$_2$OH (0.190 mL, 2.00 mmol) in THF (25 mL) was added NaH (80 mg, 60% dispersion in mineral oil, 2.00 mmol) and the resulting suspension stirred for 1 h. A solution of 32 (636 mg, 1.00 mmol) in THF (25 mL) was then added and the resulting solution stirred at room temperature for 16 h. The solvents were then removed in vacuo and the residue dissolved in methanol (25 mL) before the addition of NaOMe (cat) and stirring of the resulting suspension for 16 h. The solvents were removed in vacuo and the residue purified by flash column chromatography (normal phase, ICN silica, 50 g, 18-32µ, gradient 2.5-15% ethanol in DCM, residue dry loaded, product eluted in 7.5-10% ethanol) and twice by reverse phase prep HPLC (Phenomenex Synergi, RP-Hydro 150×10 cm$^3$, 10µ, 20 mL per min, gradient 5-40% acetonitrile in water over 10 min, product eluted in 35% acetonitrile) and (Phenomenex Synergi, RP-Hydro 150× 10 cm$^3$, 10µ, 20 mL per min, gradient 20-40% acetonitrile in water over 10 min) to yield [(3aR,4R,6R,6aR)-6-(6-amino-2-(2,2-difluoroethoxy)-9H-purin-9-yl)tetrahydrofuro[3,4-d] [1,3]dioxol-4-yl]methanol 11 as a white solid (14 mg, 4%).

HPLC (Phenomenex Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 3.88 min, 100%.

LCMS (Phenomenex Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 4.44 min, 100%, ES$^+$: 360.389 [MH]$^+$.

Example 3

Preparation of [(3aR,4R,6R,6aR)-6-(6-amino-2-(2,5-difluorophenoxy)-9H-purin-9-yl)tetrahydrofuro[3,4-d][1,3]dioxol-4-yl]methanol 12

To a solution of 2,5-difluorophenol (182 mg, 1.40 mmol) in THF (5 mL) was added KO$^t$Bu (157 mg, 1.40 mmol) and the resulting suspension stirred for 30 min before being added to a solution of 32 (445 mg, 0.70 mmol) in THF (10 mL). Stirring was continued for 3d and the solvents were then removed in vacuo. The residue was dissolved in methanol (15 mL), NaOMe (cat.) was added and the resulting mixture was stirred for 16 h, before being concentrated in vacuo and purified by flash column chromatography (normal phase, ICN silica, 50 g, 18-32μ, gradient 2-10% ethanol in DCM, residue dry loaded) and by reverse phase column chromatography (LiChroprep RP-18, 40-63 μm, 230×26 (50 g), 30 mL per min, gradient 0-100% methanol in water over 45 min, product eluted in 66% methanol) and by reverse phase prep HPLC (Phenomenex Synergi, RP-Hydro 150×10 cm$^3$, 10μ, 20 mL per min, gradient 10-100% acetonitrile in water over 10 min, product eluted in 40% acetonitrile) to yield [(3aR,4R,6R,6aR)-6-(6-amino-2-(2,5-difluorophenoxy)-9H-purin-9-yl)tetrahydrofuro[3,4-d][1,3]dioxol-4-yl]methanol 12 as a white solid (25 mg, 9%).

HPLC (Phenomenex Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 4.72 min, 98.86%.

LCMS (Phenomenex Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 5.13 min, 100%, ES$^+$: 408.418 [MH]$^+$.

Example 4

Preparation of [(3aR,4R,6R,6aR)-6-(6-amino-2-{[4'-(trifluoromethyl)biphenyl-3-yl]oxy}-9H-purin-9-yl)tetrahydrofuro[3,4-d][1,3]dioxol-4-yl]methanol 13

To a mixture of 10% Pd/C (cat), 3-iodophenol (220 mg, 1.00 mmol) and 4-(trifluoromethyl)phenylboronic acid (284 mg, 1.49 mmol) was added a solution of K$_2$CO$_3$ (415 mg, 3.01 mmol) in water (10 mL) and the reaction mixture was heated in a Biotage microwave (170° C., absorption high, pre-stirring 10 s) for 20 min. The crude reaction mixture was then extracted into EtOAc (40 mL×3) and dried over MgSO$_4$ to yield 3-(4-(trifluoromethyl)phenyl)phenol as a yellow solid (212 mg, 89%, 99% purity by HPLC) which was used without further purification.

To a solution of 3-(4-(trifluoromethyl)phenyl)phenol (119 mg, 0.50 mmol) in THF (5 mL) was added KO$^t$Bu (56 mg, 0.50 mmol) and the resulting suspension stirred for 30 min before being added to a solution of 32 (212 mg, 0.33 mmol) in THF (15 mL). Stirring was continued for 2d and the solvents were then removed in vacuo. The residue was dissolved in methanol (30 mL), NaOMe (cat.) was added and the resulting mixture was stirred for 16 h, before being concentrated in vacuo and purified by flash column chromatography (normal phase, ICN silica, 50 g, 18-321, gradient 0-10% ethanol in DCM, residue dry loaded) and by reverse phase prep HPLC (Phenomenex Synergi, RP-Hydro 150×10 cm$^3$, 10μ, 20 mL per min, gradient 5-100% acetonitrile in water over 10 min, product eluted in 100% acetonitrile) to yield [(3aR,4R,6R,6aR)-6-(6-amino-2-{[4'-(trifluoromethyl)biphenyl-3-yl]oxy}-9H-purin-9-yl)tetrahydrofuro[3,4-d][1,3]dioxol-4-yl]methanol 13 as a white solid (45 mg, 26%).

HPLC (Phenomenex Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 6.14 min, 99.39%.

LCMS (Phenomenex Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 6.41 min, 100%, ES+: 515.943 [MH]+.

Example 5

Preparation of ((3aR,4R,6R,6aR)-6-{6-amino-2-[3,5-bis(trifluoromethyl)phenyl]-9H-purin-9-yl}tetrahydrofuro[3,4-d][1,3]dioxol-4-yl)methanol 14

Scheme 5

To a solution of 2-iodo adenosine (10.0 g, 25.4 mmol) in DMF (60 mL) was added imidazole (1.73 g, 25.4 mmol) and TBDMSCl (3.83 g, 25.4 mmol) and stirring continued for 3 h. The resulting solution was quenched with aq. NaHCO$_3$ (30 mL) and extracted into ethyl acetate (250 mL) and the organic phase was washed with brine (100 mL) and water (60 mL×3) and dried over MgSO$_4$. DCM (40 mL) was then added and the resulting suspension was filtered to yield a white solid which was washed with DCM (80 mL) to afford 33 (5.20 g, 40%).

A solution of NaOH (30.9 g, excess) in water (60 mL) was added drop-wise to a solution of dibromomethane (21.4 mL, 308 mmol), 33 (5.20 g, 10.3 mmol) and tetrabutylammonium bromide (70 mg, cat.) in DCM (150 mL) and the resulting solution heated at 40° C. for 48 h. The organic layer was then separated and washed with water (×5) and dried over MgSO$_4$ to yield 34 which was used without further purification.

To a solution of 34 (assume 10.0 mmol) in THF (50 mL) was added TBAF (10.0 mL, 1M solution in THF, 10.0 mmol) and stirring continued for 2 h before concentration in vacuo. Purification by flash column chromatography (normal phase, ICN silica, 50 g, 18-32μ, gradient 0-15% ethanol in DCM, residue dry loaded, product eluted in 5-10% ethanol) afforded 35 as a white solid (750 mg, 19%) free from tetrabutylammonium salts.

A suspension of 35 (750 mg, 1.85 mmol), 3,5-bis(trifluoromethyl)phenylboronic acid (573 mg, 2.22 mmol), cesium carbonate (1.32 g, 4.44 mmol) and Pd(PPh$_3$)$_4$ (214 mg, 0.18 mmol) in ethanol (4 mL) and toluene (2 mL) was heated in a Biotage microwave (130° C., absorption high, pre-stirring 30 s) for 40 min in 2 batches which were then combined. The solvents were removed in vacuo and the residue dissolved in EtOAc (160 mL), washed with sat. aq. NaHCO$_3$ (50 mL×2) and brine (50 mL) and dried over MgSO$_4$. Purification by flash column chromatography (normal phase, ICN silica, 50 g, 18-32μ, gradient 5-10% ethanol in DCM, product eluted in 10% ethanol) and recrystallisation from hot ethanol (×2) afforded ((3aR,4R,6R,6aR)-6-{6-amino-2-[3,5-bis(trifluoromethyl)phenyl]-9H-purin-9-yl}tetrahydrofuro[3,4-d][1,3]dioxol-4-yl)methanol 14 as a white crystalline solid in 2 batches (158 mg and 85 mg, overall yield 27%).

HPLC (Phenomenex Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 6.55 min, 99.37%.

LCMS (Phenomenex Synergi, RP-Hydro, 150×4.6 mm, 4 u, 1.5 mL per min, 30° C., gradient 5-100% acetonitrile (+0.085% TFA) in water (+0.1% TFA) over 7 min—held for 30 s, 200-300 nm): Retention time 6.80 min, 100%, ES+: 492.37 [MH]+.

Active Metabolites

Structures of the expected in vivo active metabolites, corresponding to the pro-drugs described in Examples 1 to 5 are given in Table I below.

TABLE I

| Prodrug Example No. | Active metabolite Structure | Reference |
|---|---|---|
| 1 | [structure: adenosine with 2-OMe substituent] | WO 2005/084653 Compound 1 (Spongosine) |
| 2 | [structure: adenosine with 2-O-CH2-CHF2 substituent] | WO 2005/084653 Compound 2 |
| 3 | [structure: adenosine with 2-O-(2,5-difluorophenyl) substituent] | WO 2005/084653 Compound 9 |
| 4 | [structure: adenosine with 2-O-(3-(4'-trifluoromethylbiphenyl)) substituent] | |
| 5 | [structure: adenosine with 2-(3,5-bis(trifluoromethyl)phenyl) substituent] | |

Biological Methods

The Pharmacokinetics of adenosine derivatives was studied in vivo using JV-cannulated SD rats. Dose samples were either of a single compound in a suitable formulation, or a mix of 5-7 varied compounds. The animals were dosed IV (n=4) and PO via gavage tube (n=4), and blood samples (200 μl) taken at pre-dose, 5, 10, 20, 30, 45, 60, 120, 240, 360 min (IV) or pre-dose, 5, 10, 20, 45, 60, 120, 240, 360, 1440 min (PO). Samples were taken into EDTA anti-coagulant and centrifuged. The resultant plasma was stored at −80° C. prior to analysis.

Plasma was extracted either by solid phase extraction or by protein precipitation. After drying, reconstitution in appropriate solvent, centrifugation and isolation of the supernatant, the samples (n=3: IV and PO) were analyzed by High Performance Liquid Chromatography-Mass Spectrometry, using MS/MS Selected Reaction Monitoring for optimum sensitivity and selectivity. The plasma drug levels were mathematically analyzed using a non-compartmental PK calculation, with AUC's derived by the linear trapezoidal method. Half-lives were calculated by a best-fit to the terminal phase as adjudged by the user.

Results: For a range of five 2-substituted adenosines, the oral bioavailability was found to increase on average from 19% to 53% and the oral half-life from 1.3 h to 3.2 h by employing a 2',3'-methylidene acetal pro-drug strategy (Pro-drugs according to Examples 10-14).

Consequently, it is believed that by using the novel pro-drug strategies described herein, the oral bioavailability and oral half-life of these adenosine derivatives can be significantly increased. This is particularly surprising, since nucleoside derivatives tend to be polar molecules with high polar surface areas (PSAs) (e.g. adenosine 140 Å$^2$, guanosine 160 Å$^2$, cytidine 131 Å$^2$, uridine 125 Å$^2$). PSA has been shown to be a very good descriptor characterising drug absorption, including intestinal absorption, bioavailability, Caco-2 permeability and blood-brain barrier penetration. PSAs are calculated computationally using molecular topology, based on the summation of tabulated surface contributions of polar fragments (Ertl, Rohde and Selzer, J. Med. Chem. (2000) 43, 3714).

Palm et al. (Pharm. Res. (1997) 14, 568) have demonstrated a Boltzmann sigmoidal fit of PSA values to human F % over a wide range of structures and have demonstrated that typically, in order for compounds to be at least 20% bioavailable, the PSA should be <120 Å$^2$ and for at least 50% oral bioavailability, the PSA should be <95 Å$^2$.

The 2',3'-methylidene acetal pro-drugs described herein have an average calculated PSA of 125 Å$^2$ and are therefore expected to be ~15-20% orally bioavailable. The observed average oral bioavailability is surprisingly 53%.

Example 6

The anti-allodynic potential of orally administered spongosine was determined using rats experiencing streptozocin-induced diabetic neuropathy. Diabetes was induced by a single i.p. injection of 50 mg/kg streptozocin (Sigma, 50 mg/ml/kg in citrate buffered saline 33 mM pH 4.5). Control animals received single i.p. injection of citrate buffered saline. Static allodynia and diabetes could be detected from day 7 post STZ injection and were present in the majority of animals by day 14 with animals consistently demonstrating a paw withdrawal threshold (PWT) to the previously innocuous 3.63 g or lower force. Static allodynia was tested by touching the plantar surface of hind paws with Von Frey hairs (Semmes Weinstein series) in ascending order of force (0.7, 1.2, 1.5, 2, 3.6, 5.5, 8.5, 11.8, 15.1, and 29 g) for up to 6 s. The anti-allodynic potential of spongosine (0.6-2.08 mg/kg po) orally administered was examined in STZ diabetic animals once static allodynia had developed (between 20-35 days post streptozocin injection).

FIG. 1 shows that spongosine exhibited dose dependant effects (0.6-2.1 mg/kg, po) on the reversal of streptozocin induced static allodynia. All doses were effective at reversing allodynia, whilst the top dose fully reversed the allodynia to levels exhibited by naïve non-streptozocin injected control animals. Static allodynia was assessed using von Frey hairs and the paw withdrawal threshold (PWT) in grams (symbols represent the median and vertical bars represent the first and third quartiles) is indicated. All doses of spongosine tested alleviated static allodynia resulting in an increase in the PWT i.e. in the ability of the animal to withstand increased pressure exerted by the von Frey hairs. **p<0.01, *p<0.05 significantly different (Mann-Whitney U test) comparing drug treated STZ group to vehicle treated STZ group at each time point. Significant alleviation of allodynia was still evident in the 2.1 mg/kg dose cohort at 2, 3 and 4 hours.

The invention claimed is:

1. A compound having the Formula III, or a pharmaceutically acceptable salt thereof, wherein R4 is selected from OR2, NR2R3, CN, SR2 or R2; and wherein R2 and R3 are independently selected from H, $C_{1-6}$-alkyl, $C_{3-8}$-cycloalkyl, aryl or heterocyclyl, each optionally substituted with 1-3 substituents independently selected from halogen, OH, $NH_2$, CN or $CF_3$.

2. A compound according to claim 1 selected from:
[(3aR,4R,6R,6aR)-6-(6-amino-2-methoxy-9H-purin-9-yl)tetrahydrofuro[3,4-d][1,3]dioxol-4-yl]methanol;
[(3aR,4R,6R,6aR)-6-(6-amino-2-(2,2-difluoroethoxy)-9H-purin-9-yl)tetrahydrofuro[3,4-d][1,3]dioxol-4-yl]methanol;
[(3aR,4R,6R,6aR)-6-(6-amino-2-(2,5-difluorophenoxy)-9H-purin-9-yl)tetrahydrofuro[3,4-d][1,3]dioxol-4-yl]methanol;
[(3aR,4R,6R,6aR)-6-(6-amino-2-{[4'-(trifluoromethyl)biphenyl-3-yl]oxy}-9H-purin-9-yl)tetrahydrofuro[3,4-d][1,3]dioxol-4-yl]methanol; and
((3aR,4R,6R,6aR)-6-{6-amino-2-[3,5-bis(trifluoromethyl)phenyl]-9H-purin-9-yl}tetrahydrofuro[3,4-d][1,3]dioxol-4-yl)methanol.

3. A pharmaceutical formulation containing a compound according to claim 1 or 2 as active ingredient, in combination with a pharmaceutically acceptable carrier, excipient, or diluent.

* * * * *